United States Patent [19]

Baumann

[11] 4,372,317

[45] Feb. 8, 1983

[54] METHOD OF INSTALLING A SCALP ANCHOR FOR A HAIRPIECE

[75] Inventor: Jack Baumann, Los Angeles, Calif.

[73] Assignee: Look International Enterprises, Inc., San Francisco, Calif.

[21] Appl. No.: 744,151

[22] Filed: Nov. 22, 1976

Related U.S. Application Data

[62] Division of Ser. No. 625,383, Oct. 24, 1975.

[51] Int. Cl.³ ............................................. A61B 17/00
[52] U.S. Cl. ........................................... 128/330; 3/1
[58] Field of Search ........................ 3/1; 128/330, 1 R

[56] References Cited

U.S. PATENT DOCUMENTS

| | | | |
|---|---|---|---|
| 3,739,402 | 6/1973 | Cooley et al. ........................... | 3/1.5 |
| 3,826,241 | 7/1974 | Bucalo ................................. | 128/1 R |
| 3,858,247 | 1/1975 | Bauman ..................................... | 3/1 |
| 3,942,195 | 3/1976 | Bauman ..................................... | 3/1 |

*Primary Examiner*—Michael H. Thaler
*Attorney, Agent, or Firm*—Fulwider, Patton, Rieber, Lee & Utecht

[57] ABSTRACT

Removably located within an elongated epithelium-lined tract (tunnel) surgically formed in the subcutaneous layer of the scalp is the elongated subdermal portion of a scalp anchor. Mounted on at least one end of the subdermal member is a flange or tab, closely overlying the subjacent surface of the scalp, the flange being attachable to an overlying hairpiece. A plurality of such anchors securely yet removably retains the hairpiece in the desired position on the scalp.

11 Claims, 14 Drawing Figures

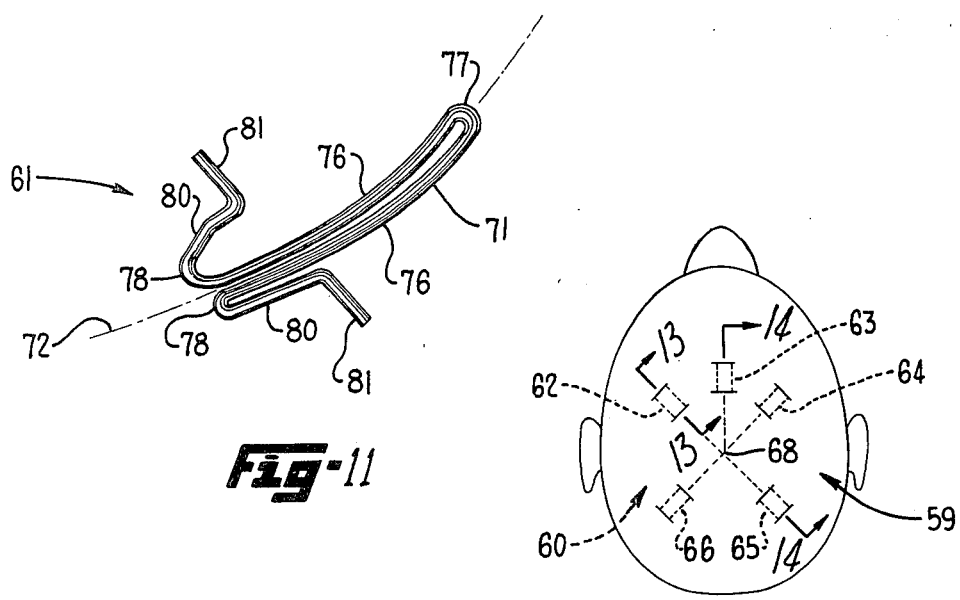
Fig-11
Fig-12
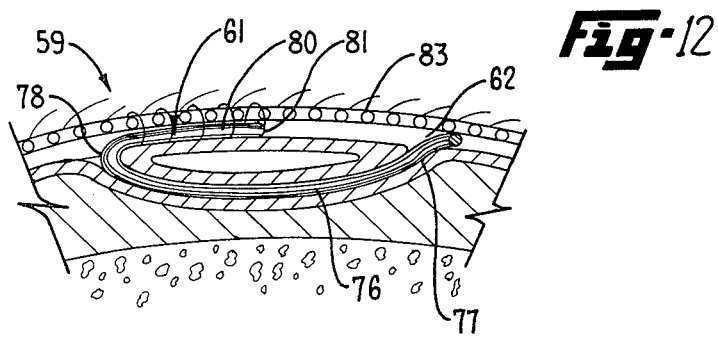
Fig-13
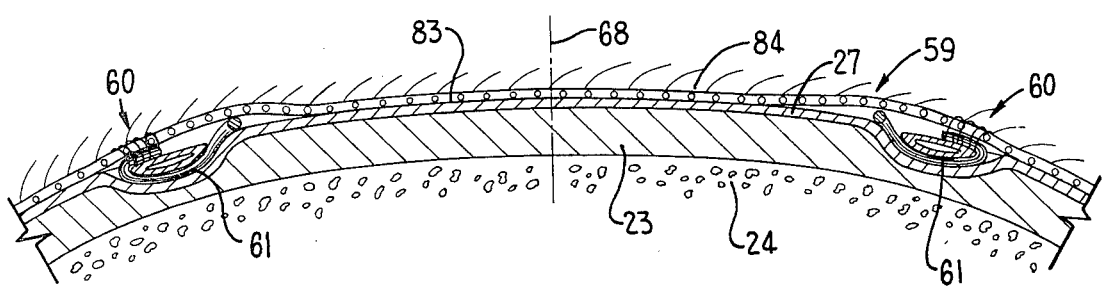
Fig-14

METHOD OF INSTALLING A SCALP ANCHOR FOR A HAIRPIECE

REFERENCE TO RELATED APPLICATIONS

This application is a division of, Ser. No. 625,383, filed on Oct. 24, 1975.

BACKGROUND OF THE INVENTION

Surgically installed scalp anchors for hairpieces are not unknown in the patent literature, exemplary being the disclosure in my U.S. Pat. No. 3,553,737.

Although the structures and procedures set forth in the foregoing patent have served quite satisfactorily in actual use, there is room for improvement, particularly in facilitating placement and removal of a hairpiece while, at the same time, affording a secure, reliable and comfortably fitting installation capable of being worn for extended periods of time.

SUMMARY OF THE INVENTION

The invention relates to improvements in anchors for removably securing a hairpiece to the scalp and to an improved method for installing such anchors.

It is an object of the invention to provide a scalp anchor which is small in size, unobtrusive in appearance and comfortable to wear, yet is reliable and secure under all normal conditions of use.

It is another object of the invention to provide a hairpiece anchor which is relatively economical yet is durable and long-lived.

It is further object of the invention to provide a scalp anchor which can readily be installed and, as quickly, can be removed when desired.

It is another object of the invention to provide a generally improved scalp anchor for a hairpiece and an improved method for installing scalp anchors.

Other objects, together with the foregoing, are attained in the embodiments described in the following description and shown in the accompanying drawings, in which:

FIG. 11 is a perspective view, to a greatly enlarged scale, of a wire clip form of scalp anchor;

FIG. 12 is a top plan view, to a reduced scale, of a scalp in which five tracts have surgically been installed;

Figure 1:
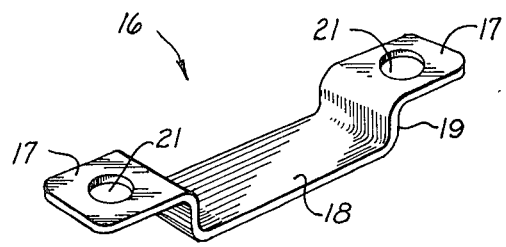
FIG. 1 is a perspective view, to a greatly enlarged scale, of a stylized form of a scalp anchor, constructed, for example, of a subdermal implant material, such as "Silastic;"

FIG. 13 is a fragmentary vertical sectional view of a scalp tract, to a greatly enlarged scale, taken on the line 13—13 in FIG. 12, and showing a wire clip form of anchor located within the tract, the clip being secured to the base fabric of a hairpiece; and, FIG. 14 is a fragmentary vertical sectional view, at approximately actual size, showing a portion of a hairpiece installed on the scalp with two of the end wire clips oriented in opposite directions and lodged within their respective registering scalp tracts, the plane of the section being indicated by the line 14—14 in FIG. 12.

While the hairpiece scalp anchor of the invention is susceptible of numerous physical embodiments, depending upon the environment, requirements of use and personal preferences of the wearer, substantial numbers of the herein shown and described embodiments have been made and tested with very satisfactory results.

In the somewhat stylized arrangement depicted in FIGS. 1-4, one form of the scalp anchor of the invention, generally designated by the reference numeral 16, includes a shaped elongated strip of subdermal implant material of any suitable make, such as "Silastic" manufactured by Dow Corning Corp. of Midland, Mich.

Exemplary approximate dimensions of the FIGS. 1-4 scalp anchor are as follows: thickness, 1 mm; width, 5 mm; overall length (including the length of the two end flanges 17, or tabs), 2.5 cm; length of central web 18, 1.5 cm; length of each tab 17, 5 mm; vertical offset 19 of each tab, 3 mm; and overall height, 5 mm.

In each tab 17 an opening 21 is provided to receive threads (not shown) or other suitable attachment means for securing the anchor 16 to the customary cross-woven fabric base of a hairpiece. The precise manner of attachment of the scalp anchor to the hairpiece can vary considerably and since the attachment, as such, forms no direct part of the present invention, it is not described in detail.

The "Silastic" scalp anchor 16 shown in FIG. 1 is implanted in the scalp 22 and, more particularly, in the subcutaneous layer 23 of skin covering the skull 24. A spaced pair of incisions 26 is made in the epidermis 27, or outer layer of skin, the incisions being slightly in excess of the 5 mm width of the anchor 16, and being spaced apart approximately 1.5 cm, i.e., the length of the central web 18.

Surgical techniques, including the use of a local anesthetic are rigidly adhered to throughout.

Figure 3:
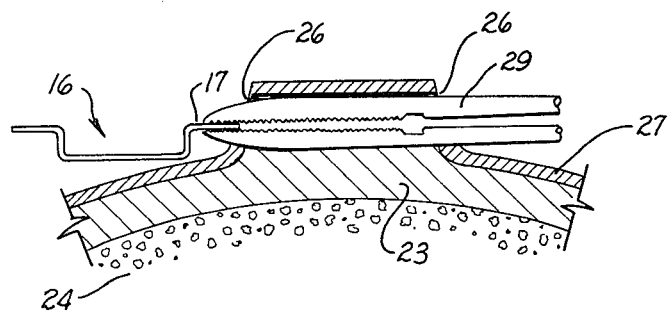
FIG. 3 is a view comparable to FIG. 2, but showing a small hemostat, or forceps, inserted through the slots to grasp one end of the scalp anchor shown in FIG. 1, and elevating the epidermal layer above the subcutaneous tissue preparatory to being withdrawn so as to implant the anchor in the subcutaneous tissue.
Figure 4:
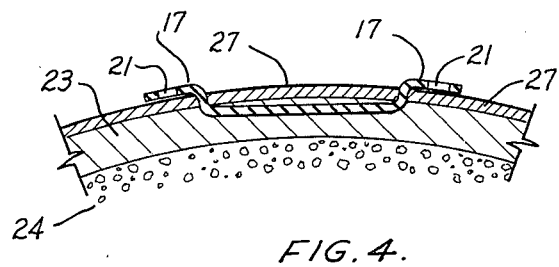
FIG. 4 is a view comparable to FIG. 2, but showing the implated anchor in position.

Following the incisions, a pair of forceps 29, or a hemostat, shown to an enlarged scale, for clarity, in FIG. 3, is inserted through one incision and out the other far enough to grip one of the tabs 17. The anchor gripping instrument 29 is thereupon withdrawn and the scalp anchor 16 is released upon reaching the desired implanted position, as shown in FIG. 4.

In due time, such as a month to 6 weeks, an epithelial layer of tissue forms around the implant, with the result that a relatively tough enclosure, or tunnel, or tract, for the scalp anchor is provided. The two exposed tabs 17 (see FIG. 4) with the openings 21 therein closely overlie the epidermis and afford a sturdy comfortable attachment for a hairpiece. The interfacial area between the anchor and the encompassing walls of the tract is considerable, thereby reducing the unit pressure imposed by random forces acting on the hairpiece.

Figure 5:
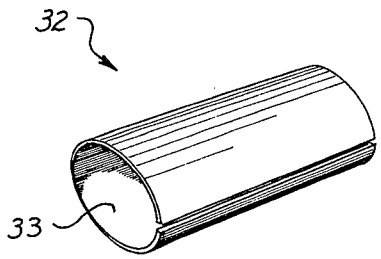
FIG. 5 is a perspective view, to a greatly enlarged scale, of a split thickness of skin rolled into tubular configuration.

The above-described implant process is facilitated, and the tract formed much more quickly, by utilizing a split-thickness skin technique wherein a very small, thin, rectangular sheet of skin, obtained from the user's thigh, back, or other appropriate planar skin surface, by well-recognized surgical procedures, is rolled into a flattened tubular configuration, as shown in stylized manner in FIG. 5, and designated by the reference numeral 32.

Figure 6:
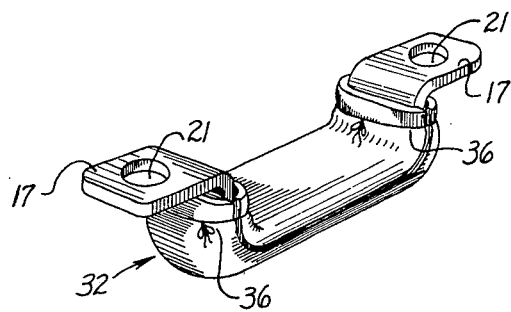
FIG. 6 is a view comparable to FIG. 1, but with the skin tube of FIG. 5 secured to the anchor.

The split skin "tube" 32 is wrapped around the anchor 16 so that the epithelial layer 33 is on the inside of the "tube" in face to face engagement with the central web 18 and the upstanding ends 19 of the anchor. Suture-formed loops 36 secure the tube 32 to the anchor, as shown most clearly in FIG. 6.

Figure 2:
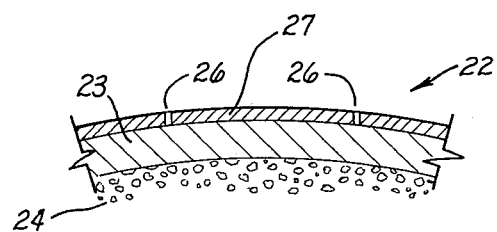
FIG. 2 is a fragmentary sectional view, to an enlarged scale, of a stylized representation of the skin overlying a scalp, the epidermal layer being incised to form a spaced pair of slots.
Figure 7:
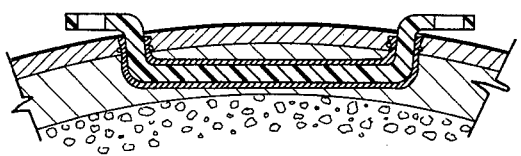
FIG. 7 is a view comparable to FIG. 4 but with the skin-covered anchor of FIG. 6 in installed position.
Figure 8:
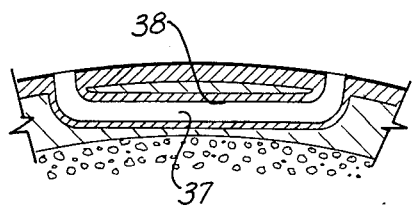
FIG. 8 is a view comparable to FIG. 7 but showing the tract, or tunnel, lined with epithelium after removal of the anchor.

Substantially the same technique is employed as in FIGS. 2-4 to lodge the split thickness skin-covered anchor in place, as appears in FIG. 7. Within a very short time, such as 2 or 3 weeks, or so, the implanted tube 32 merges with the surrounding tissues in such a manner that if the "Silastic" anchor 16 were to be thereafter removed, a tract 37, or tunnel, lined with epithelium 38, would remain, as appears most clearly in FIG. 8.

As is well-recognized, epithelial tissue is relatively tough and moderately insensitive to pain, with the result that appropriately configured scalp anchors of "Silastic" or other skin-compatible material can be reinserted in the tract 37, at will, with confidence and assurance that the anchor will be securely and comfortably retained in position. An especially strong tract is afforded if the incision is lined with two strips of full thickness skin grafts with the two strips arranged so that the epithelial tissues are face to face.

Figure 9:
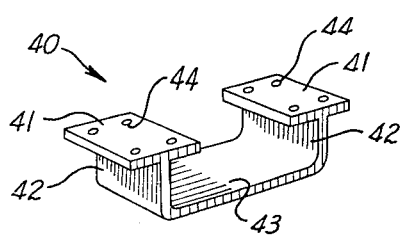
FIG. 9 is a view comparable to FIG. 1, but showing a modified form of anchor.
Figure 10:
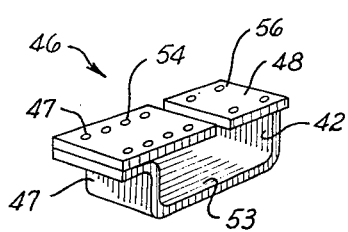
FIG. 10 is a view comparable to FIG. 9 but showing still another modified form of anchor.

FIGS. 9 and 10 illustrate variant forms of the "Silastic" strip, or band, type of anchor heretofore shown and described, noting that other tissue compatible material can also be used. FIG. 9 shows an anchor 40 with a flange 41, or tab, on each upstanding end portion 42 of the central web 43, the tabs 41 forming symmetrical T-shaped configurations. In each tab there is provided a plurality of apertures 44 to receive threads (not shown), or other attaching means, for securing the hairpiece to the anchor 40. The anchor 46 depicted in FIG. 10 is similar to the form of anchor device shown in FIG. 9 except that the flanges 47 and 48, or tabs, are of different size and are asymmetrically arranged on the respective upstanding portions 51 and 52 of the central web 53. As before, apertures 54 in the tab 47 and apertures 56 in the tabs 48 afford securing points for threads (not shown) fastened to the fabric base of the superposed hairpiece.

FIGS. 11-14 illustrate still another embodiment of the invention wherein a plurality of small, yet tough and resistant sockets 60, or receptacles, is provided in the scalp 59 to receive a plurality of respective clip-type anchors 61.

Each of the sockets 60 is, as before, surgically formed, with the use of a local anesthetic. Either the split skin thickness or the twin full thickness skin graft technique is followed so as to provide, quickly and safely, a plurality of elongated epithelium-lined tracts, or tunnels 62, 63, 64, 65 and 66 (see FIG. 12) oriented so that their axes converge in a location 68 substantially centrally disposed on top of the scalp.

Since most dynamic forces, such as wind and water, tending to dislodge a hairpiece come from the front, more anchor sockets are preferably disposed forward of the transverse center line through the geometrical center 68 than aft thereof.

As appears most clearly in FIG. 11, the removeable, clip-type of anchor 61 includes a tissue-compatible wire 71 which is symmetrical about a fore and aft axis 72. Arranged in substantially parallel relation is a pair of arcuately bowed, side by side, spaced apart, fore and aft portions 76 joining at their recurved forward end 77, the after ends 78 of the bowed wire portions 76 being recurved upwardly and forwardly throughout the portions 80 for approximately one half the length of the bowed portion 76, then flaring laterally outwardly in planar fashion to form a pair of wings 81, or tabs, which overlie, in snug relation, the top of the exposed skin of the scalp, as appears most clearly in FIGS. 13 and 14. The spacing between the portions 76 affords an air channel connecting the tunnel with the outside so that air can circulate into and out of the tunnel.

The bowed parallel wire portions 76 are downwardly concave in side elevation except for the forwardmost end 77 which protrudes somewhat from the tract (see FIGS. 13 and 14) for even greater security against being dislodged by vertical stress components, and can readily be inserted in the respective similarly arcuately bowed tracts previously provided in the scalp by surgical means.

The divergent wings 81 and the associated arcuately convex portions 80 afford convenient tabs to which threads from the hairpiece base 83, of woven network or fabric material, can be secured.

By orienting all of the sockets 60 toward the central point of convergency 68, and by correspondingly locating and orienting the clip-type anchors 61 on the hairpiece 84, the wearer can readily place the hairpiece in the appropriate location on the scalp so that the individual clips 61 can be inserted in that respective sockets 60. Thereafter, any force tending to slide or otherwise move the hairpiece in any direction along the top of the scalp will encounter effective resistance and opposition from one or more of the anchors. Secure placement of the hairpiece is thereby afforded.

Yet, should the wearer decide to remove the hairpiece for any reason, finger manipulation of the individual clips 61 will readily effect withdrawal of the concavely bowed portions 76 from the respective sockets 60.

As will be appreciated, the clip form of anchor although readily lending itself to fabrication from stainless steel wire, can also be formed, to advantage, from a stamping, as from thin, stainless steel sheet or strip strip stock.

It can therefore be seen that I have provided an economical and versatile yet efficient scalp anchor and method of installing scalp anchors for securely yet releasably retaining a hairpiece.

What is claimed is:

1. A method of forming anchorage means on the scalp to enable removable installation of a hairpiece, said method comprising forming a pair of spaced incisions in the scalp, removing from another surface of the body at least one sheet of skin, transplanting and inserting said sheet of skin within the scalp with the normally outwardly directed surface of said sheet of skin directed inwardly and away from the adjacent scalp tissue which said sheet of skin overlies, so that said sheet of skin substantially defines an area extending between said incisions, thereafter leaving said sheet of skin in such position until it merges with the adjacent scalp tissue to form an integral tunnel open at its opposite ends and throughout its entire length, said tunnel extending continuously between said incisions and being adapted to removably receive a scalp anchor for attachment of a hairpiece to said scalp anchor.

2. The method described in claim 1, which includes securing said sheet of skin to an elongated member having greater rigidity than said sheet of skin, and then inserting said elongated member beneath the scalp so that said elongated member extends continuously between said incisions with its opposite ends extending outwardly through said incisions.

3. The method described in claim 2, which includes winding said sheet of skin around said elongated member so as to substantially completely enclose said elongated member prior to inserting said elongated member beneath the scalp.

4. The method described in claim 1, which includes inserting a tool through one of said incisions and beneath the epidermis of the scalp to draw said sheet of skin through the other of said incisions.

5. The method described in claim 1, wherein said sheet of skin is a split-thickness skin.

6. The method described in claim 1, which includes lining the area between said incisions with at least one strip of skin, said skin being arranged with its epithelial tissue disposed in face-to-face relationship to comprise the inner lining of said tunnel.

7. The method described in claim 1, which includes forming a plurality of said tunnels in the scalp, with the longitudinal axes of all of said tunnels being directed toward a common center adjacent to the center of the top of the scalp.

8. The method described in claim 1 wherein said sheet of skin is a full thickness skin.

9. The method described in claim 1 including the steps of locating and orienting a clip-type anchor on a hairpiece, placing the hairpiece on the scalp and inserting the clip of the anchor into said tunnel.

10. The method described in claim 9 including forming a plurality of said tunnels in the scalp, locating a like number of said anchors on said hairpiece, and inserting the clip of each of said anchors in respective ones of said tunnels.

11. The method described in claim 10 including forming said tunnels with their longitudinal axes directed toward a common center adjacent to the center of the top of the scalp.

* * * * *